United States Patent
Madhav et al.

(10) Patent No.: US 9,976,991 B2
(45) Date of Patent: May 22, 2018

(54) OPTICAL GAS SENSOR

(71) Applicants: Kalaga Venu Madhav, Bangalore (IN); Swapnil Sushilendra Deshpande, Pune (IN); Abhijeet Vikram Kshirsagar, Pune (IN); Chinmaya Rajiv Dandekar, Pune (IN); Yogesh Shinde, Pune (IN); Sarin Kumar Anakkat Koyilothu, Bangalore (IN)

(72) Inventors: Kalaga Venu Madhav, Bangalore (IN); Swapnil Sushilendra Deshpande, Pune (IN); Abhijeet Vikram Kshirsagar, Pune (IN); Chinmaya Rajiv Dandekar, Pune (IN); Yogesh Shinde, Pune (IN); Sarin Kumar Anakkat Koyilothu, Bangalore (IN)

(73) Assignee: Cooper Technologies Company, Houston, TX (US)

( * ) Notice: Subject to any disclaimer, the term of this patent is extended or adjusted under 35 U.S.C. 154(b) by 298 days.

(21) Appl. No.: 14/844,773

(22) Filed: Sep. 3, 2015

(65) Prior Publication Data
US 2016/0061784 A1 Mar. 3, 2016

Related U.S. Application Data

(60) Provisional application No. 62/045,222, filed on Sep. 3, 2014.

(51) Int. Cl.
*G01N 29/24* (2006.01)
*G01N 21/17* (2006.01)
(Continued)

(52) U.S. Cl.
CPC ..... *G01N 29/2425* (2013.01); *G01N 21/1702* (2013.01); *G01N 29/022* (2013.01);
(Continued)

(58) Field of Classification Search
CPC .................................. G01N 29/2425
See application file for complete search history.

(56) References Cited

U.S. PATENT DOCUMENTS 4,557,603 A * 12/1985 Oehler ............... G01N 21/0303
250/343
7,069,769 B2 * 7/2006 Kung ................... G01N 21/05
73/23.2
(Continued)

FOREIGN PATENT DOCUMENTS

CN 2831348 Y 10/2006
GB 2396405 6/2004
(Continued)

OTHER PUBLICATIONS

I. Zhestovskaya, Search Report and Written Opinion issued in International Application No. PCT/US2015/048359, completion date Dec. 24, 2015, dated Jan. 14, 2016, 6 pages, Federal Institute of Industrial Property, Moscow, Russia.
(Continued)

*Primary Examiner* — Paul West
*Assistant Examiner* — Mark A Shabman
(74) *Attorney, Agent, or Firm* — King & Spalding LLP

(57) ABSTRACT

A sensor head is described herein. The sensor head can include a first piece, where the first piece can include a body having an outer surface and an inner surface. The first piece can also include a light source cavity disposed in the body at the inner surface. The first piece can further include an optical device cavity disposed in the body at the inner surface. The first piece can also include an ellipsoidal cavity disposed in the body at the inner surface, where the ellipsoidal cavity is disposed adjacent to the optical device cavity. The first piece can further include a receiving device cavity disposed in the body adjacent to the inner surface that forms the ellipsoidal cavity. The first piece can also include at least one channel disposed in the body.

20 Claims, 6 Drawing Sheets

(51) Int. Cl.
  *G01N 29/22* (2006.01)
  *G01N 29/02* (2006.01)
  *G01N 29/036* (2006.01)

(52) U.S. Cl.
  CPC ......... *G01N 29/036* (2013.01); *G01N 29/222* (2013.01); *G01N 2021/1704* (2013.01); *G01N 2201/0637* (2013.01); *G01N 2291/021* (2013.01); *G01N 2291/0427* (2013.01)

(56) References Cited

U.S. PATENT DOCUMENTS

| | | | |
|---|---|---|---|
| 8,117,897 B2 | 2/2012 | Schropp, Jr. et al. | |
| 2014/0367574 A1* | 12/2014 | Lin | G01N 21/3504 250/343 |

FOREIGN PATENT DOCUMENTS

| | | |
|---|---|---|
| JP | 0936460 | 2/1997 |
| RU | 2109269 C1 | 4/1998 |
| WO | 2006071171 | 7/2006 |

OTHER PUBLICATIONS

Machine Translation of CN 2831348 Y, via Lexis Nexis Total Patents, 4 pages.
Machine Translation of 2109269 C1, via Lexis Nexis Total Patents, 11 pages.

* cited by examiner

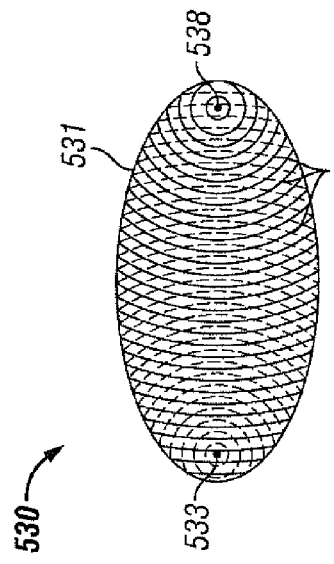
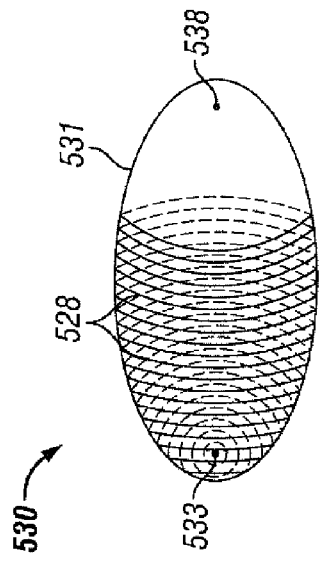
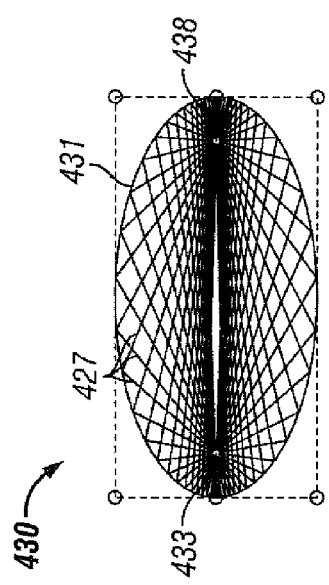
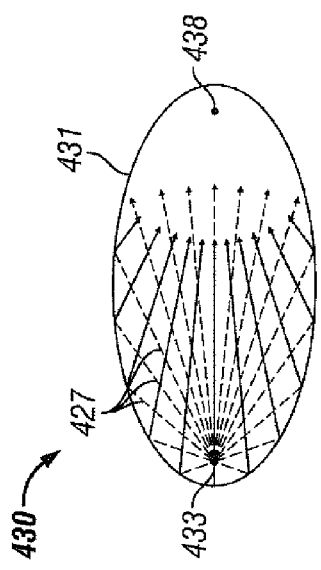

OPTICAL GAS SENSOR

CROSS REFERENCE TO RELATED APPLICATIONS

This application claims priority under 35 U.S.C. § 119 to U.S. Provisional Patent Application Ser. No. 62/045,222, titled "Optical Gas Sensor" and filed on Sep. 3, 2014, the entire contents of which are hereby incorporated herein by reference.

TECHNICAL FIELD

Embodiments described herein relate generally to gas sensors, and more particularly to systems, methods, and devices for optical gas sensors.

BACKGROUND

The detection and measurement of gas concentrations is important for both the understanding and monitoring of a wide variety of applications, such as environmental monitoring, industrial process control analysis, combustion processes, detection of toxic and flammable gases, as well as explosives. For example, gas sensors capable of high sensitivity and selectivity can be used in atmospheric science for the detecting and monitoring of different gas species including greenhouse gases and ozone, and in breath diagnostics, for detection and monitoring of nitric oxide, ethane, ammonia and numerous other biomarkers. As another example, in gas-to-grid applications, methane generated from a bio process is tested for impurities (e.g., hydrogen sulfide or $H_2S$) to determine whether the methane is pure enough to be mixed directly with natural gas.

SUMMARY

In general, in one aspect, the disclosure relates to a sensor head having a first piece. The first piece can include a body having an outer surface and an inner surface, and a light source cavity disposed in the body at the inner surface, where the light source cavity is disposed at a first end of the body and is configured to receive a light source. The first piece can also include an optical device cavity disposed in the body at the inner surface, where the optical device cavity is disposed adjacent to the light source cavity and is configured to receive an optical device. The first piece can further include an ellipsoidal cavity disposed in the body at the inner surface, where the ellipsoidal cavity is disposed adjacent to the optical device cavity. The first piece can also include a receiving device cavity disposed in the body adjacent to the inner surface that forms the ellipsoidal cavity, where the receiving device cavity is configured to receive a receiving device. The first piece can further include at least one channel disposed in the body, wherein the at least one channel has a first end disposed at the inner surface adjacent to the ellipsoidal cavity.

In another aspect, the disclosure can generally relate to an optical gas sensor that includes at least one piece of a sensor head. The at least one piece of the sensor head can include a body having an outer surface and an inner surface, and a light source cavity disposed in the body at the inner surface, where the light source cavity is disposed at a first end of the body. The at least one piece of the sensor head can also include an optical device cavity disposed in the body at the inner surface, where the optical device cavity is disposed adjacent to the light source cavity. The at least one piece of the sensor head can further include an ellipsoidal cavity disposed in the body at the inner surface, where the ellipsoidal cavity is disposed adjacent to the optical device cavity, and where the ellipsoidal cavity comprises a first focus point and a second focus point. The at least one piece of the sensor head can also include a receiving device cavity disposed in the body adjacent to the inner surface that forms the ellipsoidal cavity. The at least one piece of the sensor head can further include a first channel disposed in the body, where the first channel has a first end disposed at the inner surface forming the ellipsoidal cavity. The optical gas sensor can also include a light source disposed within the light source cavity, an optical device disposed within the optical device cavity, and a receiving device disposed within the receiving device cavity.

These and other aspects, objects, features, and embodiments will be apparent from the following description and the appended claims.

BRIEF DESCRIPTION OF THE DRAWINGS

The drawings illustrate only example embodiments of optical gas sensors and are therefore not to be considered limiting of its scope, as optical gas sensors may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

FIGS. 4A and 4B show the disbursement of optical waves within the ellipsoidal cavity in accordance with certain example embodiments.

FIGS. 5A and 5B show the disbursement of acoustic waves within the ellipsoidal cavity in accordance with certain example embodiments.

DETAILED DESCRIPTION OF EXAMPLE EMBODIMENTS

Figure 1:
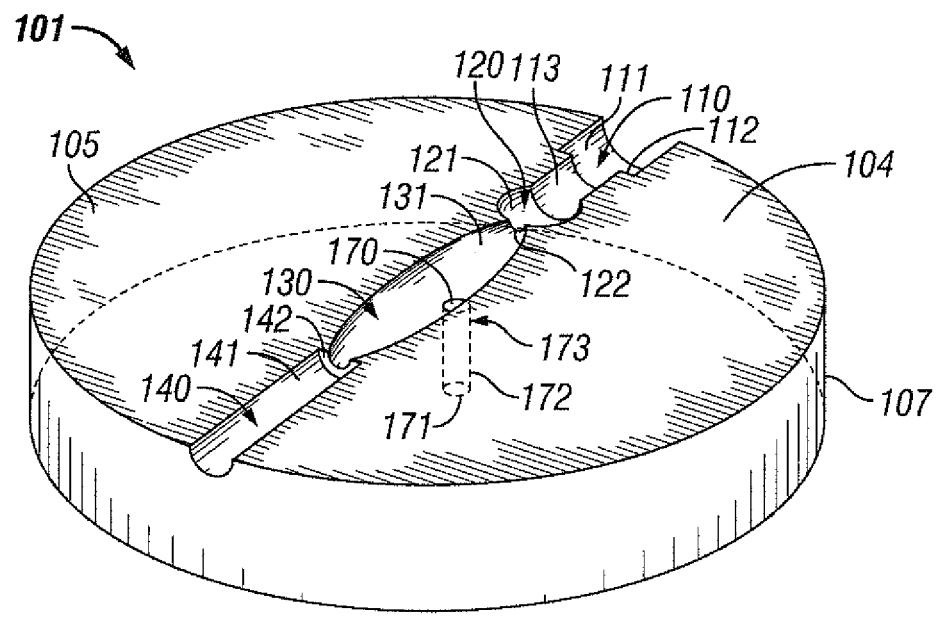
FIG. 1 shows a top perspective view of a portion of a sensor head in accordance with certain example embodiments.

The example embodiments discussed herein are directed to systems, apparatuses, and methods related to optical gas sensors. Optical gas sensors can have a number of configurations and use a number of technologies. For example, a quartz-enhanced photo-acoustic spectroscopic (QEPAS) sensor can have an optical irradiation at a gas-specific wavelength directed through a gap between the prongs of a quartz tuning fork (QTF) vibrating at its resonating frequency. The optical energy is absorbed and released by the gas, causing a change in the resonant frequency of the QTF. The amount of change in the resonant frequency of the QTF is proportional to the concentration of the gas molecules. As described herein, a QTF can also be called a tuning fork.

As another example, an example optical gas sensor can modulate light (e.g., laser) wave excitation frequency such that the test gas produces acoustic waves with a frequency that match a resonance frequency, as for a QTF or other receiving device. As the gas concentration increases, the amplitude of the acoustic waves increases, which in turn increases the oscillations of the receiving device. One or more components (e.g., a lock-in amplifier) can be used to amplify the signal (e.g., the acoustic waves) at substantially only the resonant frequency, which can improve the signal-to-noise (SNR) ratio. As yet another example, an example optical gas sensor can use one or more microphones. In other words, example embodiments described herein are not limited to use with a certain technology, such as with respect to receiving devices.

While example embodiments are described herein as being directed to optical gas sensors, example embodiments can also be used with other types of sensors. Further, optical gas sensors that can be used with example embodiments can have any of a number of configurations not shown or described herein. As described herein, a user can be any person that interacts with example optical gas sensors. Examples of a user may include, but are not limited to, a consumer, an operations specialist, a gas engineer, a supervisor, a consultant, a contractor, an operator, and a manufacturer's representative.

In one or more example embodiments, example caps for optical gas sensors are subject to meeting certain standards and/or requirements. For example, the International Electrotechnical Commission (IEC) sets standards, such as IEC 60079-28 that applies to optical gas sensors, with which example caps must comply to be used in field applications. Examples of other entities that set applicable standards and regulations include, but are not limited to, the National Electrical Manufacturers Association (NEMA), the National Electric Code (NEC), the Institute of Electrical and Electronics Engineers (IEEE), and Underwriters Laboratories (UL).

In some cases, the example embodiments discussed herein can be used in any type of hazardous environment, including but not limited to an airplane hangar, a drilling rig (as for oil, gas, or water), a production rig (as for oil or gas), a refinery, a chemical plant, a power plant, a mining operation, a wastewater treatment facility, and a steel mill. The caps for optical gas sensors (or components thereof) described herein can be physically placed in and/or used with corrosive components (e.g., gases). In addition, or in the alternative, example caps for optical gas sensors (or components thereof) can be subject to extreme heat, extreme cold, moisture, humidity, dust, and other conditions that can cause wear on the caps for optical gas sensors or portions thereof.

In certain example embodiments, the caps for optical gas sensors, including any components and/or portions thereof, are made of one or more materials that are designed to maintain a long-term useful life and to perform when required without mechanical and/or other types of failure. Examples of such materials can include, but are not limited to, aluminum, stainless steel, fiberglass, glass, plastic, ceramic, and rubber.

Any components (e.g., inlet tube coupling feature, receiving channel) of example caps for optical gas sensors, or portions thereof, described herein can be made from a single piece (as from a mold, injection mold, die cast, or extrusion process). In addition, or in the alternative, a component (or portions thereof) can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, fastening, securing, abutting, or other similar terms. Such terms are merely meant to distinguish various elements and/or features within a component or device and are not meant to limit the capability or function of that particular element and/or feature. For example, a feature described as a "coupling feature" can couple, secure, fasten, abut, and/or perform other functions aside from, or in addition to, merely coupling.

A coupling feature (including a complementary coupling feature) as described herein can allow one or more components (e.g., a wall that forms an ellipsoidal cavity) and/or portions of optical gas sensors to become mechanically and/or electrically coupled, directly or indirectly, to another portion of the optical gas sensor. A coupling feature can include, but is not limited to, a clamp, a portion of a hinge, an aperture, a recessed area, a protrusion, a slot, a spring clip, a tab, a detent, a threaded coupling, and mating threads. One portion of an example optical gas sensor can be coupled to another portion of the optical gas sensor by the direct use of one or more coupling features. In addition, or in the alternative, a portion of an example optical gas sensor can be coupled to another portion of the optical gas sensor using one or more independent devices that interact with one or more coupling features disposed on a component of the optical gas sensor. Examples of such devices can include, but are not limited to, a pin, a hinge, a fastening device (e.g., a bolt, a screw, a rivet), and a spring.

One coupling feature described herein can be the same as, or different than, one or more other coupling features described herein. A complementary coupling feature as described herein can be a coupling feature that mechanically couples, directly or indirectly, with another coupling feature. For any figure shown and described herein, one or more of the components may be omitted, added, repeated, and/or substituted. Accordingly, embodiments shown in a particular figure should not be considered limited to the specific arrangements of components shown in such figure.

Any component described in one or more figures herein can apply to any other (e.g., subsequent) figures having the same label. In other words, the description for any component of a different (e.g., subsequent) figure can be considered substantially the same as the corresponding component described with respect to another (e.g., previous) figure. The numbering scheme for the components in the figures herein are such that each component is represented by a three or four digit number, where substantially similar components between figures are represented by a number having the identical last two digits. As such, a figure having a substantially similar feature as a different figure can rely on the description and/or reference number of the substantially similar feature associated with the different figure.

Example embodiments of optical gas sensors will be described more fully hereinafter with reference to the accompanying drawings, in which example optical gas sensors are shown. Optical gas sensors may, however, be embodied in many different forms and should not be construed as limited to the example embodiments set forth herein. Rather, these example embodiments are provided so that this disclosure will be thorough and complete, and will fully convey the scope of optical gas sensors to those of ordinary skill in the art. Like, but not necessarily the same, elements (also sometimes called components) in the various figures are denoted by like reference numerals for consistency.

Terms such as "top", "bottom", "left", "right", "inner," "outer," "end," "portion", "first", and "second" are used merely to distinguish one component (or part of a component or state of a component) from another. Such terms are not meant to denote a preference or a particular orientation. Also, the names given to various components described herein are descriptive of example embodiments and are not meant to be limiting in any way. Those skilled in the art will appreciate that a feature and/or component shown and/or described in one embodiment (e.g., in a figure) herein can be used in another embodiment (e.g., in any other figure) herein, even if not expressly shown and/or described in such other embodiment.

FIG. 1 shows a top-side perspective and semi-transparent view of a top portion of a sensor head 101 in accordance with certain example embodiments. The top portion of the sensor head 101 in this case is a single piece that includes a body 104 having an inner surface 105, an outer surface (hidden from view) opposite the inner surface 105, and at least one side 107. The top portion of the sensor head 101 can have any of a number of shapes and sizes. For example, the portion of the sensor head 101 shown in FIG. 1 is cylindrical in shape. The portion of the sensor head 101 can be made from one or more of a number of suitable materials, including but not limited to stainless steel and nickel-based alloys. The material of the portion of the sensor head 101 can be resistant to one or more of a number of corrosive materials, including but not limited to hydrogen sulfide ($H_2S$) gas.

In certain example embodiments, a number of cavities are disposed in the body 104 at the inner surface 105. For example, a light source cavity 110 can be formed by a light source cavity wall 111, a light source cavity wall 113, and a collar 112 disposed therebetween. The light source cavity 110 can have a shape and size to host one or more of a number of light sources (as shown and described below with respect to FIG. 3). The light source cavity 110 can be disposed at any location along the inner surface 105. For example, as shown in FIG. 1, the light source cavity 110 can be disposed at one end (e.g., close to the side 107) of the top portion of the sensor head 101.

As another example, an optical device cavity 120 can be formed by an optical device cavity wall 121 and a collar 122. The optical device cavity 120 can have a shape and size to host one or more of a number of optical devices (as shown and described below with respect to FIG. 3). The optical device cavity 120 can be disposed at any location along the inner surface 105. For example, as shown in FIG. 1, the optical device cavity 120 can be disposed adjacent to the light source cavity 110 so that optical device cavity wall 121 is adjacent to the light source cavity wall 113.

As yet another example, an ellipsoidal cavity 130 (sometimes referred to more simply herein as a cavity 130) can be formed by an ellipsoidal cavity wall 131. The ellipsoidal cavity 130 can have a shape and size sufficient to receive and reflect light emitted from a light source multiple times and mix the reflected light with gas disposed in the ellipsoidal cavity 130. The ellipsoidal cavity 130 can be disposed at any location along the inner surface 105. For example, as shown in FIG. 1, the ellipsoidal cavity 130 can be disposed adjacent to the optical device cavity 120 so that the ellipsoidal wall 131 is adjacent to the collar 122. Gas can be disposed in the ellipsoidal cavity 130 through one or more channels 173 disposed in the body 104 of the top portion of the sensor head 101. In this case, there is only one channel 173, and the channel 173 has a first end 171 at the outer surface, and a second end 170 at the ellipsoidal cavity wall 131, and a channel wall 172 disposed therebetween. The first end 171 can also be at the side 107. A channel 173 can be linear, curved, angled, and/or have one or more of any other shapes.

As still another example, a receiving device cavity 140 can be formed by a tuning fork cavity wall 141 and a collar 142. The receiving device cavity 140 can have a shape and size to host one or more of a number of tuning forks (as shown and described below with respect to FIG. 3). The receiving device cavity 140 can be disposed at any location along the inner surface 105. For example, as shown in FIG. 1, the receiving device cavity 140 can be disposed adjacent to the ellipsoidal cavity 130 so that the collar 142 is adjacent to the ellipsoidal cavity wall 131. In addition, the receiving device cavity 140 can be disposed at another end (e.g., close to the side 107) of the top portion of the sensor head 101. In such a case, the receiving device cavity 140 can be located at an opposite end of the top portion of the sensor head 101 relative to the light source cavity 110.

In certain example embodiments, the light source cavity 110, the optical device cavity 120, the ellipsoidal cavity 130, and the receiving device cavity 140 can be aligned substantially linearly with each other and have a common axis that runs along the length of each cavity. In certain example embodiments, there are multiple portions of the sensor head. For example, there may be two symmetrical pieces of the sensor head, where one piece is the top portion of the sensor head 101 shown in FIG. 1. In such a case, when the two pieces are joined together, the various cavities become enclosed and walls become substantially continuous.

Figure 2:
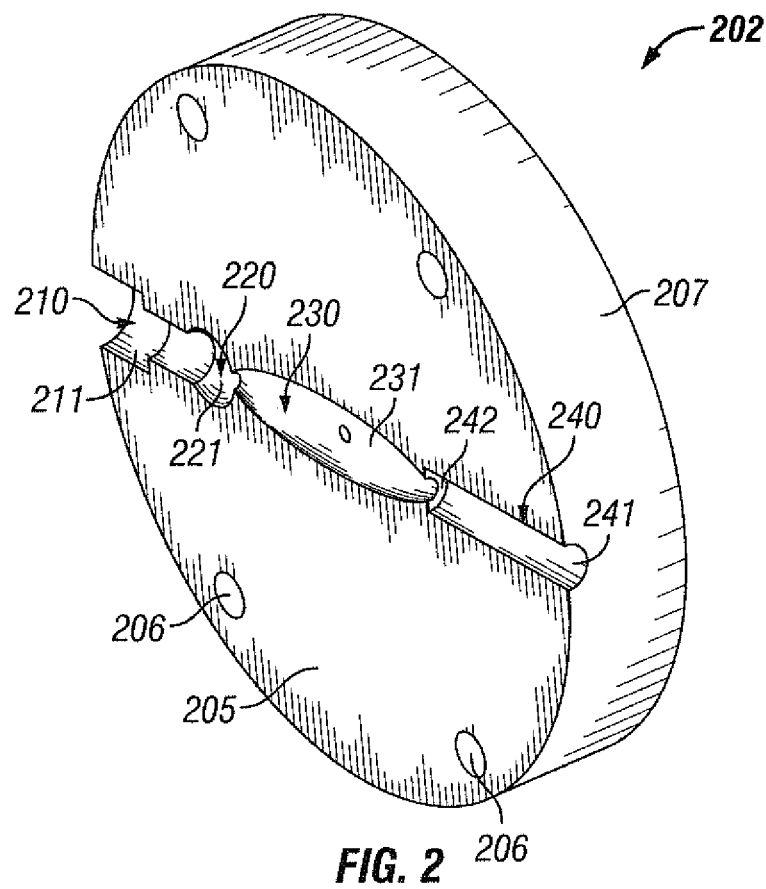
FIG. 2 shows a top perspective view of a portion of another sensor head in accordance with certain example embodiments.

FIG. 2 shows a side-top perspective view of a portion of a sensor head 202 in accordance with certain example embodiments. Referring to FIGS. 1 and 2, the bottom portion of a sensor head 202 of FIG. 2 is substantially the same as the top portion of the sensor head 101 of FIG. 1, except as described below. The bottom portion of the sensor head 202 of FIG. 2 includes a number of coupling features 206 (in this case, apertures) that allow the bottom portion of the sensor head 202 to become coupled, directly or indirectly, to another symmetrically configured portion of the sensor head, such as the top portion of the sensor head 101. Further, in this case, the bottom portion of the sensor head 202 of FIG. 2 does not include any channel, such as channel 173 of FIG. 1.

Figure 3:
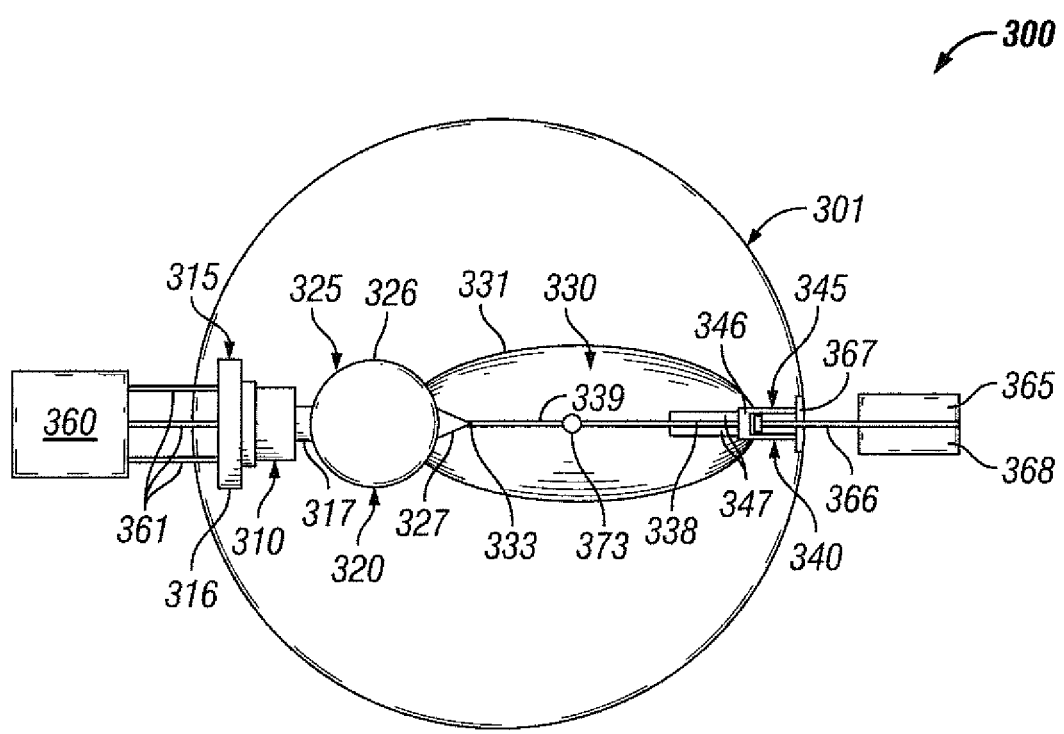
FIG. 3 shows a cross sectional side view of a sensor in accordance with certain example embodiments.

FIG. 3 shows a cross sectional top view of a sensor subassembly 300 in accordance with certain example embodiments. Put another way, FIG. 3 shows a top view of a top portion of the sensor head 301 of the sensor subassembly 300, with a light source 315 disposed in the light source cavity (hidden from view by the light source 315), an optical device 325 disposed in the optical device cavity (hidden from view by the optical device 325), and a receiving device 345 (in this case, a tuning fork 345) disposed in the receiving device cavity 340 (hidden from view by the tuning fork 345).

Referring to FIGS. 1-3, the light source 315 can use any type of lighting technology (e.g., light emitting diode, a laser diode (also called a semiconductor laser)) that generates light 317 that is directed toward the optical device 325. The light source 315 can have a shape and size that conforms to one or more contours of the light source cavity 310. The light 317 generated and emitted by the light source 315 can be of any suitable wavelength, depending on one or more of a number of factors, including but not limited to the gas being tested, the temperature, and the characteristics of the optical device 325. The light source 315 can be coupled to a power source 360 (e.g., a driver), which can provide power and/or control signals to the light source 315. The light source 315 can include one or more of a number of components, including but not limited to a light element (e.g., a diode, a bulb) and a circuit board.

In certain example embodiments, the optical device 325 is any type of device capable of receiving light 317 from the light source 315 and processing the light 317 to create light 327 that is transmitted to a particular location within the ellipsoidal cavity 330. The optical device 325 can have an outer surface 326 that abuts against some or all of the wall 121 and the collar 122 that forms the optical device cavity 320 in the portion of the sensor head 301. The optical device 325 can have any shape (e.g., sphere, semi-sphere, pyramid) and size that conforms to one or more contours of the optical device cavity 320.

The optical device 325 can be made of one or more suitable materials, including but not limited to silica and glass. In any case, the optical device 325 is resistant to corrosive materials, such as $H_2S$ gas. In order for the optical device 325 to transmit the light 327 to a particular location (in this case, focal point 333) within the ellipsoidal cavity 330, a number of factors must be balanced. Such factors can include, but are not limited to, the orientation of the optical device 325, the material of the optical device 325, the position of the optical device 325 relative to the ellipsoidal cavity 330 and the light source 315, and the wavelength of the light 317. In certain example embodiments, a sealing member (e.g., a gasket, an o-ring, silicone) can be used to provide a barrier that prevents potentially corrosive materials in the ellipsoidal cavity 330 from entering the optical device cavity 320 or the light source cavity 310.

The ellipsoidal cavity 330 has one or more walls 331 that are optically and acoustically reflective. If the ellipsoidal cavity 330 is formed by more than one piece of a sensor head 301, then the pieces are highly machined so that the junctions where the multiple pieces meet within the ellipsoidal cavity 330 provide little to no substantial degradation of the optical and acoustic reflective uniformity relative to the rest of the walls 331 of the ellipsoidal cavity 330. In certain example embodiments, the ellipsoidal cavity 330 has two focus points (in this case, focus point 333 and focus point 338) that are positioned along the major axis 339 of the ellipsoidal cavity 330. In some cases, as shown in FIG. 3, the major axis 339 of the ellipsoidal cavity 330 can extend along the substantial center of the optical cavity 320, the light source cavity 310, and/or the receiving device cavity 340.

In certain example embodiments, the light 327 transmitted from the optical device 325 is directed to focus point 333 within the ellipsoidal cavity 330. In such a case, the light (optical waves) passes through the focus point 333 and are reflected off of the wall 331 at least one time to converge at focus point 338 within the ellipsoidal cavity 330. An example of how the optical waves from the light 327 travel from focus point 333 to focus point 338 within the ellipsoidal cavity 330 is shown in FIGS. 4A and 4B below.

Also disposed within the ellipsoidal cavity 330 in certain example embodiments is a gas. The gas can consist of one or more elements (e.g., carbon, hydrogen) that can combine to form one or more compounds (e.g., methane). In some cases, the gas can also have impurities (e.g., $H_2S$) that can be detected, both in existence and in amount, using example embodiments. As discussed above, the gas can be injected into the ellipsoidal cavity 330 through one or more channels (e.g., channel 172) disposed in the body 304 of the sensor head 301, entering the ellipsoidal cavity 330 through the second end 370 (also called a gas entry port 370). When the gas molecules interact with the light waves (derived from light 327) reflected off the wall 331 in the ellipsoidal cavity 330, the gas molecules become stimulated.

Each second end 370 of a channel can be disposed at any point on the wall 331 forming the ellipsoidal cavity 330. For example, as shown in FIG. 3, the second end 370 of a channel 372 can be positioned at a point on the wall 331 between the focus point 333 and the focus point 338, when viewing the ellipsoidal cavity 330 from a side view. In such a case, the gas emitted through the second end 370 can more easily interact with the reflected light waves within the ellipsoidal cavity 330.

As discussed below, when the receiving device 345 is a tuning fork, the tines 347 of the tuning fork, disposed in the receiving device cavity 340, can be positioned such that the focus point 338 is disposed between the tines 347. When the gas molecules are stimulated by the light waves in the ellipsoidal cavity 330, the amplitude of the acoustic waves associated with the gas molecules increase. When those acoustic waves reach the focus point 338, they have a frequency which substantially match the frequency at which the tines 347 vibrate. Specifically, the greater the amplitude of the acoustic waves, the greater the oscillations at which the tines 347 resonate, and this increase in oscillations of the tines 347 can be captured to determine the content of the test gas.

In certain example embodiments, the tuning fork 345 is any type of device that vibrates at one or more frequencies. The tuning fork 345 can have one or more components. For example, in this case, the tuning fork 345 has multiple (e.g., two, three, four) tines 347 and a base 346 from which the tines 347 extend. The tines 347 can be at least partially flexible, so that the shape of the tines 347 can change. When the shape of the tines 347 change, the tines can vibrate at a different frequency. The tuning fork 345 (including any of its components, such as the tines 347) can be made of any suitable material, including but not limited to quartz. In any case, the tuning fork 345 can be resistant to corrosive materials, such as $H_2S$ gas.

The tines 347 of the tuning fork 345 can be oriented in any of a number of suitable ways within the ellipsoidal cavity 330. For example, the tines 347 can be substantially parallel to major axis 339 of the ellipsoidal cavity 330, which includes the focus point 333 and the focus point 338. In certain example embodiments, a sealing member (e.g., a gasket, an o-ring, silicone) (not shown) can be used to provide a barrier that prevents potentially corrosive materials in the ellipsoidal cavity 330 from entering the receiving device cavity 340.

In certain example embodiments, the tines 347 of the tuning fork 345 can vibrate based on something other than the stimulated gas molecules within the ellipsoidal cavity 330. For example, a driver 365 can be coupled to the tuning fork 345. In such a case, the driver 365 can provide a vibration frequency to the tuning fork 345, causing the tines 347 to vibrate at a certain frequency. Such a frequency may be substantially similar to a frequency induced by a pure form (without any impurities) of the gas being stimulated within the ellipsoidal cavity 330. Alternatively, the tines 347 of the tuning fork 345 can vibrate at a resonant frequency as determined by the driver 365.

To measure the frequency at which the tines 347 of the tuning fork 345 are vibrating, one or more measuring devices can be used. For example, as shown in FIG. 3, a receiver 368 can be coupled to the tuning fork 345. In such a case, the receiver 368 can determine a vibration frequency to the tuning fork 345. Thus, when the vibration frequency of the tines 347 changes, the measured change can be directly correlated to an impurity in the gas injected through the channel into the ellipsoidal cavity 330. Alternatively, the receiver 368 can measure the oscillations of the tines 347 of the tuning fork 345 when the tines 347 vibrate at a resonant frequency.

In certain example embodiments, the driver 365 and/or the receiver 368 can be coupled to the tuning fork 345 in one or more of a number of ways. For example, as shown in FIG. 3, an adapter 367 can be mechanically coupled to the base 346 of the tuning fork 345, and one or more electric conductors 366 can be coupled between the adapter 367 and the driver and/or the receiver 368. In certain alternative embodiments, wireless technology can be used to couple the driver 365 and/or the receiver 368 to the tuning fork 345.

FIGS. 4A and 4B show the disbursement of optical waves 427 within the ellipsoidal cavity 430 in accordance with certain example embodiments. Specifically, FIG. 4A shows light waves 427 beginning to travel from focus point 433 to focus point 438, and FIG. 4B shows the light waves 427 in full reflection between focus point 433 and focus point 438. Referring to FIGS. 1-4B, the ellipsoidal cavity 430 and wall 431 of FIGS. 4A and 4B are substantially the same as the ellipsoidal cavity 330 and wall 331 of FIG. 3. The light waves 427 are derived from the light 327 transmitted by the optical device 325 and passing through the focus point 433. As can be seen, the light waves 427 are reflected off the wall 431 and converge on focus point 433 and focus point 438.

As mentioned above, the tines 347 of the tuning fork 345 can vibrate based on a signal received from the driver 365. In addition, or in the alternative, the tines 347 of the tuning fork 345 surround the focus point 338, and when the gas is stimulated by the light waves 427 within the ellipsoidal cavity 430, the vibration frequency of the tines 347 can change. In any case, as the tines 347 of the tuning fork 345 vibrate, the tines 347 radiate acoustic waves 528, as shown in FIGS. 5A and 5B. Alternatively, the acoustic waves 528 associated with the gas can have a frequency that substantially matches the resonant frequency of the tines 347 of the tuning fork 345. In such a case, as the amplitude of the acoustic waves 528 increase, the oscillations of the tines 347 resonating at the resonant frequency also increase. FIG. 5A shows acoustic waves 528 beginning to travel from focus point 538 to focus point 533, and FIG. 5B shows the acoustic waves 528 in full reflection between focus point 533 and focus point 538.

Referring to FIGS. 1-5B, the ellipsoidal cavity 530 and wall 531 of FIGS. 5A and 5B are substantially the same as the ellipsoidal cavity 330 and wall 331 of FIG. 3. The acoustic waves 528 are derived from vibration of the tines 347 of the tuning fork 345, which surround focus point 538.

As can be seen, the acoustic waves 528 are reflected off the wall 531 and converge on focus point 533 and focus point 538. The receiver 368 or similar acoustic measuring device can be used to measure the acoustic waves 528 and, consequently, determine an amount of impurity in the gas injected into the ellipsoidal cavity 530.

Figure 6:
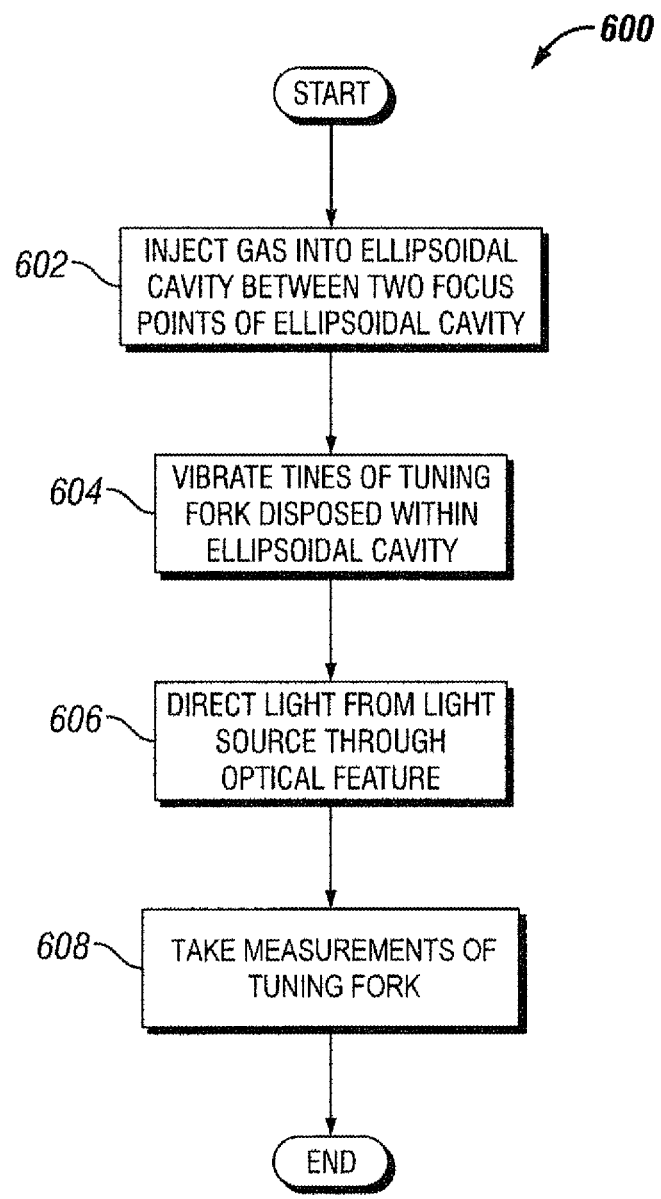
FIG. 6 shows a flowchart of a method for determining a level of impurity in a gas in accordance with certain example embodiments.

FIG. 6 shows a flowchart 600 of a method for determining a level of impurity in a gas using a tuning fork in accordance with certain example embodiments. Referring to FIGS. 1-6, in step 602 in the flowchart 600 of FIG. 6, gas is injected into an ellipsoidal cavity 330 between two focus points 333 and 338 of the ellipsoidal cavity 330. In step 604, a receiving device 345 (in this case, a tuning fork 345) is disposed within the ellipsoidal cavity 330. Alternatively, the receiving device 345 can be disposed at some location outside the ellipsoidal cavity 330, an example of which is discussed below with respect to FIGS. 8-10. Specifically, a number of tines 347 of the tuning fork 345 are disposed within the ellipsoidal cavity 330 and vibrated. The tines 347 can be disposed around a first focus point 338 of the two focus points of the ellipsoidal cavity 330. The tines 347 can be vibrated at a first rate that equates to a pure form of the gas. The tines 347 can be vibrated at the first rate by a driver 365. Alternatively, the tines 347 of the tuning fork 345 can vibrate at a resonant frequency, as determined by the driver 365. Those skilled in the art will appreciate that other receiving devices (e.g., a microphone, as discussed below) can be used in place of a tuning fork.

In step 606, light 317 from a light source 315 can be directed through an optical feature 325. The optical feature 325 can be located adjacent to the ellipsoidal cavity 330. The light 317 can be directed by the optical feature 325 as light 327 to a second focus point 333 of the two focus points within the ellipsoidal cavity 330. From the focus point 333, the light 427 can be reflected from the second focus point 333 by at least one wall 331 forming the ellipsoidal cavity 330 to the first focus point 338 of the two focus points. The light 427 can excite the gas within the ellipsoidal cavity 330. In certain example embodiments, the light source 315 and the optical feature 325 can be combined into a single component.

In step 608, measurements of the tuning fork 345 are taken. For example, a second rate of vibration of the tines 347 of the tuning fork 345 can be measured. The second rate can be based on the level of impurity of the gas. The second rate of vibration can be driven by the gas excited by the light 427. The second rate of vibration can be acoustic waves 528 that are measured by a measuring device, such as a receiver 368. As another example, the oscillations of the tines 347 of the tuning fork 345 can be measured by the receiver 368 when the tines 347 vibrate at a resonant frequency. Example embodiments can be used to increase the amplitude of the acoustic waves 528 so that the receiving device 345 can make more accurate and effective measurements as to the content of the test gas.

Figure 7:
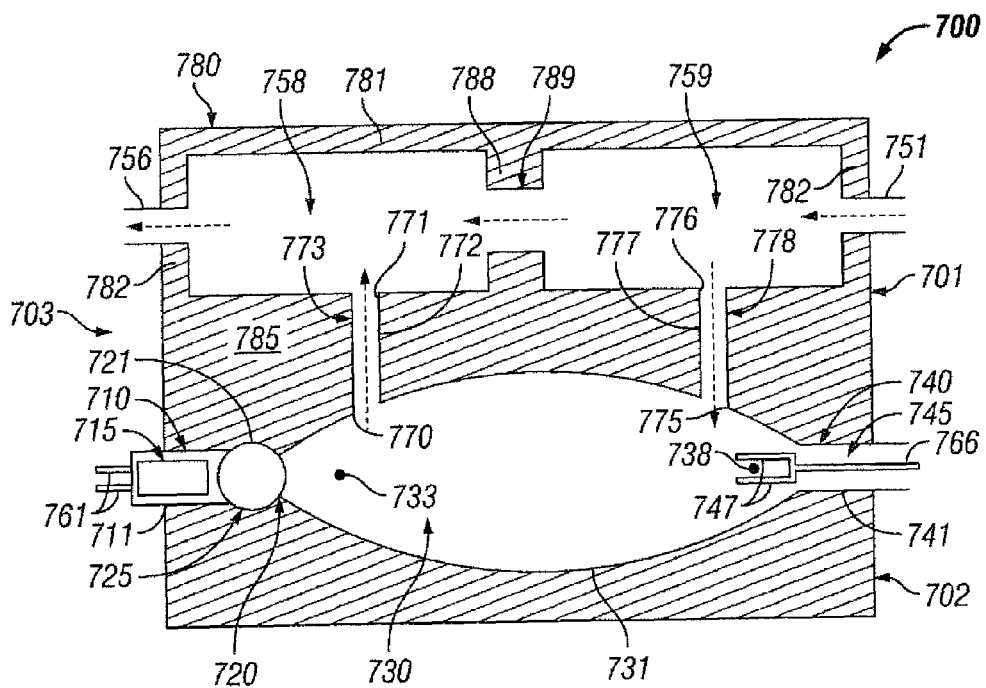
FIG. 7 shows a cross sectional side view of a sensor subassembly in accordance with certain example embodiments.

FIG. 7 shows a cross sectional side view of a sensor subassembly 700 in accordance with certain example embodiments. The sensor subassembly 700 of FIG. 7 includes a gas sensor measurement assembly 703, a light source 715, an optical device 725, and a receiving device 745 (in this case, a tuning fork 745). The gas sensor measurement assembly 703 can include a top portion of the sensor head 701 and a bottom portion of the sensor head 702, where the top portion of the sensor head 701 and the bottom portion of the sensor head 702 are coupled to each other so that the ellipsoidal cavity 730, the light source cavity 710, the optical device cavity 720, and the receiving device cavity 740 are whole and substantially continuous.

Referring to FIGS. 1-7, the bottom portion of the sensor head 702 is substantially similar to the bottom portion of the sensor head 202 of FIG. 2. Further, the top portion of the sensor head 701 of FIG. 7 is substantially similar to the top portion of the sensor head 101 of FIG. 1, except as described below. Specifically, the top portion of the sensor head 701 of FIG. 7 has two channels (channel 773 and channel 778) rather than a single channel. Channel 778 is substantially similar to channel 773. For example, channel 778 has a first end 776 at the outer surface, and a second end 775 at the ellipsoidal cavity wall 731, and a channel wall 777 disposed therebetween. Further, the light source 715, the optical device 725, and the tuning fork 745 of FIG. 7 are substantially similar to the light source 315, the optical device 325, and the tuning fork 345 described above with respect to FIG. 3.

Figure 9:
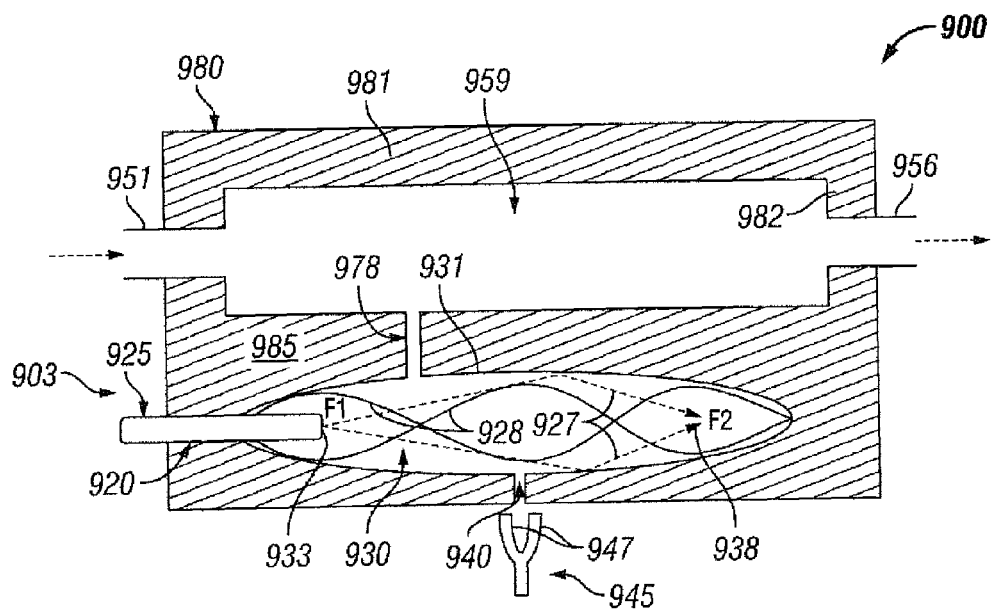
FIG. 9 shows a cross sectional side view of yet another sensor subassembly in accordance with certain example embodiments.
Figure 10:
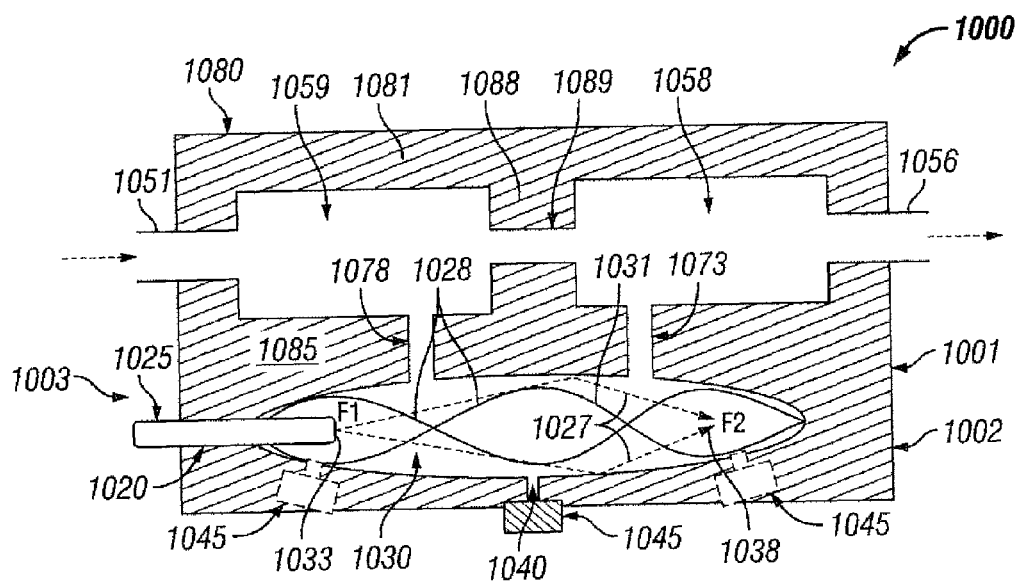
FIG. 10 shows a cross sectional side view of still another sensor subassembly in accordance with certain example embodiments.

In certain example embodiments, as shown in FIG. 7, disposed on top of the top portion of the sensor head 701 can be a cap 780. The cap 780, as well as the top portion of the sensor head 701 and the bottom portion of the sensor head 702, including any portions thereof, can be made of one or more materials that are resistant to corrosion and other harmful effects that can be caused by the test gas, the tested gas, and/or the environment in which the gas sensor measurement assembly 703 is exposed. A purpose of the cap 780 can include controlling an amount, rate, and/or other flow characteristics of test gas that is delivered into the example ellipsoidal cavity (e.g., ellipsoidal cavity 330) described herein. The cap 780 can have any of a number of configurations. An example of a configuration of the cap 780 is shown in FIG. 7. Other examples of a cap are shown in FIG. 9 and FIG. 10 below.

These configurations of the cap 780, relative to the shape and size of the ellipsoidal cavity 730 and other components (e.g., optical feature 725, light source 715) of the sensor head, can be adjusted to provide a number of benefits. For example, the specific configuration of the cap 780 can allow for easier alignment of where and how much test gas is injected into the ellipsoidal cavity 730. As another example, the specific configuration of the cap 780 can help create resonance of a receiving device 745 (such as the tines 747 of a tuning fork 745) at a certain, more precise frequency. This certainty in the frequency can improve the amplitude of the acoustic waves, which in turn can allow for more precise measurements taken by the receiving device 745.

In certain example embodiments, the gas sensor measurement assembly 703 is configured to perform any measurements of the gas being tested (also called the test gas herein). As such, the gas sensor measurement system 703 can be configured to receive the test gas and remove any gas that has been tested (also called test gas). For this to occur, the cap 780 is coupled to the top portion of the sensor head 701 in such a way that the cap 780 delivers the test gas to the top portion of the sensor head 701, and also receives the tested gas (the test gas that has been tested) from the top portion of the sensor head 701.

In certain example embodiments, the cap 780, the top portion of the sensor head 701, and the bottom portion of the sensor head 702 is formed from a single piece. Alternatively, the cap 780, the top portion of the sensor head 701, and/or the bottom portion of the sensor head 702 can be a separate piece that is coupled to one or more of the other pieces. The cap 780 can include at least one wall that forms a cavity. For example, the cap 780 in this case has a top wall 781, a side wall 782, and a bottom wall 785 that forms the cavity. The cavity can be completely enclosed, substantially enclosed, or partially enclosed. For example, if the bottom wall 785 of the cap 780 is absent, the cavity of the cap 780 would be partially enclosed.

In certain example embodiments, the cavity of the cap 780 has multiple (e.g., two, three, four) portions. For example, in this case the cavity is divided into a first cavity portion 758 and a second cavity portion 759. When the cavity of the cap 780 has multiple cavity portions, each cavity portion can be virtually or physically separated from other cavity portions of the cavity of the cap 780. For example, in this case, the first cavity portion 758 and the second cavity portion 759 are physically separated from each other by a partition 788. In such a case, the partition 788 can have or include one or more of a number of characteristics. Examples of such characteristics can include, but are not limited to, a solid configuration, a porous material, a non-porous material, a mesh, and an orifice (such as orifice 789).

When the portions of the cavity of the cap 780 are physically separated from each other by the partition 788, the partition 788 can substantially isolate one portion (e.g., cavity portion 758) from the other portions (e.g., cavity portion 759). A partition 788 can be temporary or permanent with respect to its position in the cavity of the cap 780. The partition 788 can help separate the test gas from the tested gas. The partition 788 can also help reduce and/or control the flow rate and/or turbulent flow of the test gas, which in turn can control the flow of the test gas sent to the cavity 730 of the sensor head. The partition 788 can also help regulate one or more of a number of parameters (e.g., pressure) within the cavity of the cap 780. If the cavity of the cap 780 has multiple portions, the shape and size of one portion of the cavity can be the same as, or different than, the shape and size of the other portions of the cavity. For example, in this case, cavity portion 758 can have substantially the same shape and size as the cavity portion 759.

In certain example embodiments, the cap 780 is coupled to the top portion of the sensor head 701. Alternatively, the cap 780 can be coupled to some other portion of the sensor head. If the cap 780 and the sensor head are separate pieces, the cap 780 can be coupled to the top portion of the sensor head 701 using one or more of a number of coupling features. For example, the coupling features can be one or more apertures that traverse the thickness of the cap 780 and that are disposed substantially equidistantly toward the outer perimeter of the cap 780. In such a case, each coupling feature can receive a fastening device (e.g., a bolt) that is used to couple the cap 780 to the top portion of the sensor head 701.

The characteristics (e.g., shape, size, configuration) of the coupling features can be configured to correspond to the associated characteristics of coupling features of the top portion of the sensor head 701. In such a case, the cap 780 can be coupled to the top portion of the sensor head 701 in one or more certain orientations. The cap 780 can include one or more features to accommodate the coupling features. For example, there can be a recessed area in which a coupling feature can be disposed. Each coupling feature can be disposed, at least in part, in at least one of the walls (e.g., top wall 781, bottom wall 785) of the cap 780.

In certain example embodiments, the cap 780 receives the test gas from a source (e.g., an inlet header of the gas sensor device) through the inlet tube 751. In such a case, the inlet tube 751 is coupled to some portion of the cap 780. For example, the cap 780 can include an inlet tube coupling feature that couples to the inlet tube 751. The inlet tube coupling feature can include one or more of a number of coupling features. For example, the inlet tube coupling feature can include a threaded coupling disposed at the distal end of the inlet tube 751. In such a case, the threaded coupling couples to the inlet tube 751.

The proximal end of the inlet tube 751 can be disposed within a wall (e.g., top wall 781, side wall 782, bottom wall 785) of the cap 780 so that the test gas can be delivered to the cavity of the cap 780 or a portion (e.g., cavity portion 758, cavity portion 759) thereof. Put another way, the tube 751 of the inlet tube coupling feature can be disposed in a wall (in this case, the top wall 781) of the cap 780 so that the test gas emitted through the proximal end of the tube 751 is delivered to a portion of the cavity (in this case, cavity portion 759). In such a case, the proximal end of the tube 751 can be disposed along the inner surface of a wall (e.g., the top wall 781) so that the tube 751 is adjacent to that portion of the cavity.

To deliver the test gas from the cap 780 to the top portion of the sensor head 701, at least one channel (e.g., channel 778, channel 773) can run between the cap 780 and the top portion of the sensor head 701. Each channel can be disposed, at least in part, in a wall (e.g., bottom wall 785) of the cap 780. Further, a channel can be located adjacent to a portion (e.g., cavity portion 159) of the cavity. In certain example embodiments, the channel 778 is adjacent to the same portion of the cavity (in this case, cavity portion 759) as the inlet tube 751. For example, in this case, the channel 778 and the inlet tube 751 are each located adjacent to cavity portion 159 at different positions along a wall (or, in this case, different walls) of the cap 780.

In certain example embodiments, the channel 778 transports the test gas from the cap 780 to the top portion of the sensor head 701. For example, in this case, the channel 778 is disposed in the top portion of the sensor head 701 adjacent to the ellipsoidal cavity 730. In certain example embodiments, the channel 778 (or portions thereof) can include a partition, as with the partition 788 described above with respect to the cavity of the cap 780, to help control the flow of the test gas as the test gas flows to the ellipsoidal cavity 730. Once the test gas is distributed through the channel 778 into the ellipsoidal cavity 730, the test gas is tested within the ellipsoidal cavity 730 as described above with respect to FIGS. 1-6.

To complete the circulation process involving the test gas, once the test gas is tested in the ellipsoidal cavity 730, the resulting gas (called the tested gas) is removed from the ellipsoidal cavity 730. To receive the tested gas by the cap 780 from the ellipsoidal cavity 730, one or more channels (in this case, channel 773) can be disposed between the ellipsoidal cavity 730 at the top portion of the sensor head 701 and the cavity portion 758 of the cap 780. The channel 773. Once the test gas is sent from the ellipsoidal cavity 730 to the cavity portion 758 through the channel 773, the test gas can be removed from the cavity portion 758 of the cap 780.

For example, as shown in FIG. 7, the cap 780 can include an outlet tube 756 that couples to the wall 782 adjacent to the cavity portion 758. The outlet tube 756 can include one or more of a number of coupling features. For example, the outlet tube 756 can include a threaded coupling disposed at the distal end of the outlet tube 756. In such a case, the threaded coupling couples to the wall 782 of the cap 780. The proximal end of the outlet tube 756 can be disposed within a wall (e.g., top wall 781, side wall 782, bottom wall 785) of the cap 780 so that the test gas can be removed from the cavity of the cap 780 or a portion (e.g., cavity portion 758, cavity portion 759) thereof. Put another way, the outlet tube 756 can be disposed in a wall (in this case, the side wall 781) of the cap 780 so that the tested gas can be received from a portion of the cavity (in this case, cavity portion 758) by the distal end of the outlet tube 756. In such a case, the proximal end of the tube 756 can be coupled to another portion (e.g., an outlet header) of the gas sensor device.

The channel 773 can be disposed, at least in part, in a wall (e.g., bottom wall 785) of the cap 780. Further, the channel 773 can be located adjacent to a portion (e.g., cavity portion 758) of a cavity of the cap 780. In certain example embodiments, the channel 773 is adjacent to the same portion of the cavity as the outlet tube 756. For example, in this case, the channel 773 and the outlet tube 756 are each located adjacent to cavity portion 758 at different positions along a wall (or, in this case, different walls) of the cap 780. In certain example embodiments, the channel 773 (or portions thereof) can include a partition, as with the partition 788 described above with respect to the cavity of the cap 780, to help control the flow of the tested gas as the tested gas flows from the ellipsoidal cavity 730 to the cavity portion 758 of the cap 780.

In certain example embodiments, a portion of the cavity of the cap 780 can include one or more features that channel the flow of gas (e.g., test gas, tested gas) through that portion of the cavity. Examples of such features can include, but are not limited to, contoured inner surfaces of a wall and baffles. For example, cavity portion 759 can include baffles that channel test gas that flows from the inlet tube 751 through the cavity portion 759 to the channel 778. In any case, a portion (e.g., 3%) of the test gas flowing into the cavity portion 759 from the inlet tube 751 is directed to the channel 778, while the rest (e.g., 97%) of the test gas flowing into the cavity portion 759 from the inlet tube 751 is directed through the orifice 789.

Figure 8:
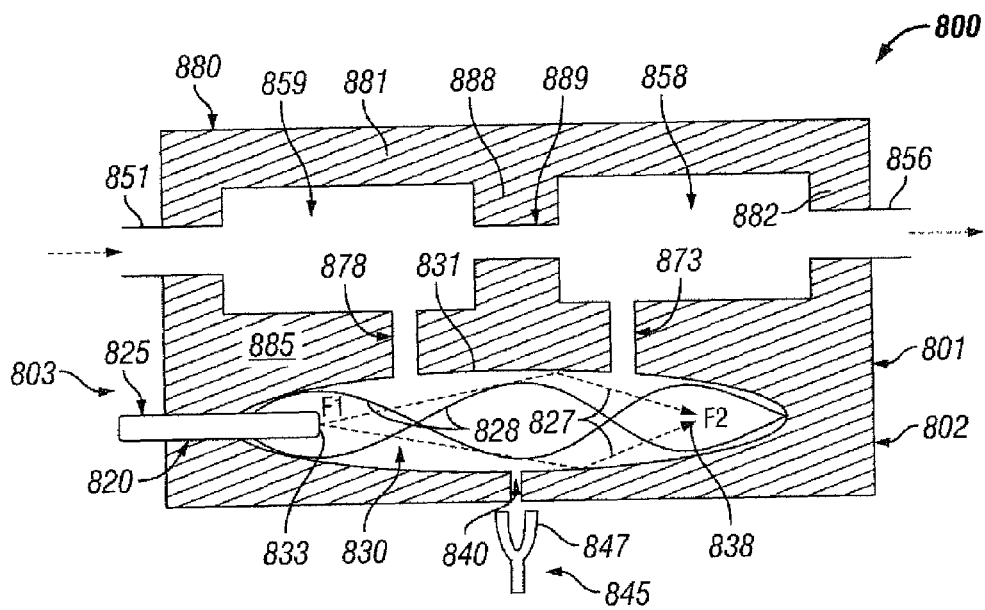
FIG. 8 shows a cross sectional side view of another sensor subassembly in accordance with certain example embodiments.

FIG. 8 shows a cross sectional side view of another sensor subassembly 800 in accordance with certain example embodiments. The sensor subassembly 800 of FIG. 8 is substantially the same as the sensor subassembly 700 of FIG. 7, except as described below. Specifically, while the receiving device 845 is still a tuning fork 845, the tuning fork 845 (including the tines 847 of the tuning fork 845) are not disposed within the ellipsoidal cavity 830. Instead, the entirety of the tuning fork 845 is disposed in the receiving device cavity 840, located adjacent to the ellipsoidal cavity 830. In other words, the receiving device cavity 840 opens into the inner surface 831 that forms the ellipsoidal cavity 830. Further, the gas flows from left to right in FIG. 8, as opposed to flowing from right to left in FIG. 7. The dimensions of the ellipsoidal cavity 830 can be chosen such way that they achieve acoustic resonance at a certain resonant frequency (e.g., the resonant frequency of the tuning fork 845). In such a case, the acoustic waves 828 can be amplified because of the resonance, which improves performance of the gas sensor.

In addition, the sensor subassembly 800 of FIG. 8 differs from the sensor subassembly 700 of FIG. 7 in that the orientation and location of the receiving device cavity 840 relative to the ellipsoidal cavity 830 has changed. Specifically, as shown in FIG. 8, the receiving device cavity 840 is disposed along the bottom of the ellipsoidal cavity 830 rather than along the right side, as shown in FIG. 7. Yet another difference between the sensor subassembly 800 of FIG. 8 and the sensor subassembly 700 of FIG. 7 is that there is a single optical device 815 in FIG. 8 that combines the light source 715 and the optical device 725 of FIG. 7. Similarly, rather than the light source coupling feature 710 and the optical device coupling feature 720 of FIG. 7, there is only an optical device coupling feature 820 in FIG. 8.

The optical device 825 coupled to the optical device coupling feature 820 can be an assembly of one or more components (e.g., lens, light source) that uses any type of optical and/or other technology (e.g., fiber optics). For example, optical device 825 can be a laser diode assembly or a fiber optic source. If the optical device 825 includes a lens, the lens can be a plano-convex lens that has a focus at some point (e.g., focus point 838) in the cavity 830. The optical device 825 can be coupled directly or indirectly to the optical device coupling feature 820. For example, the optical device 825 can include, or can be coupled to, a SubMiniature version A (SMA) connector, which in turn is coupled to the optical device coupling feature 820.

If the optical device 825 includes a light source, the light source can generate light that is directed toward the cavity 830, either directly or indirectly (e.g., through a lens) of the optical device 825. The light generated and emitted by the light source can be of any suitable wavelength, depending on one or more of a number of factors, including but not limited to the gas being tested, the temperature, and the characteristics of the lens of the optical device 825. The light source of the optical device 825 can be coupled to a power source (e.g., a driver), which can provide power and/or control signals to the light source and/or other components of the optical device 825.

The light source can include one or more of a number of components, including but not limited to a light element (e.g., a light-emitting diode, a bulb) and a circuit board. If the optical device 825 includes a lens, the lens can be capable of receiving light (e.g., from a light source) and processing the light to create light that is transmitted to a particular location within the cavity 830. The optical device 825 can have any shape (e.g., sphere, semi-sphere, pyramid) and size that conforms to one or more contours of the optical device coupling feature 820.

The optical device 825 can be made of one or more suitable materials, including but not limited to silica and glass. In any case, the optical device 825 is resistant to corrosive materials, such as H$_2$S gas. In order for the optical device 825 to transmit the light to a particular location within the cavity 830, a number of factors must be balanced. Such factors can include, but are not limited to, the orientation of the optical device 825, the material of the optical device 825, the position of the optical device 825 relative to the receiving device 345, and the wavelength of the light. In certain example embodiments, a sealing member (e.g., a gasket, an o-ring, silicone) can be used to provide a barrier that prevents potentially corrosive materials in the cavity 830 from entering the optical device coupling feature 820.

In this case, the distal end of the optical device 825 extends substantially to the focus point 833 within the ellipsoidal cavity 830. Further, since the receiving device 845 is not disposed, at least in part, in the ellipsoidal cavity 830, a portion of the test gas (the acoustic waves 828), which are stimulated by the light waves 827, must travel through the optical device coupling feature 820. In such a case, at least a portion of the optical device coupling feature 820 can be configured like a channel (e.g., channel 873, channel 878), as described above.

FIG. 9 shows a cross sectional side view of yet another sensor subassembly 900 in accordance with certain example embodiments. The sensor subassembly 900 of FIG. 9 is substantially the same as the sensor subassembly 800 of FIG. 8, except as described below. Specifically, the cap 980 of the sensor subassembly 900 of FIG. 9 has only a single cavity 959, which means that the cap 980 does not have a partition (e.g., partition 888) or orifice (e.g., orifice 889), as shown in FIG. 8. Further, there is only one channel 978 between the cavity 959 of the cap 980 and the ellipsoidal cavity 930. As a result, test gas flows in only one direction through the channel 978, from the cavity 959 of the cap 980 to the ellipsoidal cavity 930.

Because the only other option that test gas in the ellipsoidal cavity 930 can flow is through the receiving device cavity 940. Thus, at least a portion of the receiving device cavity 940 can be configured like a channel (e.g., channel 978), as described above. As with the sensor subassembly 800 of FIG. 8, the receiving device 945 (in this case a tuning fork 945) is disposed within the receiving device cavity 940 so that no part of the tuning fork 945 is disposed within the ellipsoidal cavity 930.

FIG. 10 shows a cross sectional side view of still another sensor subassembly 1000 in accordance with certain example embodiments. The sensor subassembly 1000 of FIG. 10 is substantially the same as the sensor subassembly 800 of FIG. 8, except as described below. Specifically, the receiving device 1045 of the sensor subassembly 1000 of FIG. 10 is a microphone 1045 rather than a tuning fork. FIG. 10 shows a number of positions and locations in which the microphone 1045 can be disposed relative to the ellipsoidal cavity 1030.

The sensor subassembly 1000 can have a single microphone 1045 or multiple microphones 1045. A microphone 1045 can be positioned at any location relative to the ellipsoidal cavity 1030. For example, a microphone 1045 can abut against the inner surface 1031 that forms the ellipsoidal cavity 1030. Alternatively, a microphone 1045 can be disposed, at least in part, within the ellipsoidal cavity 1030. As yet another alternative, a microphone 1045 can be integrated with the inner surface 1031 that forms the ellipsoidal cavity 1030. As still another alternative, a microphone 1045 can be completely removed from the ellipsoidal cavity 1030 by some distance.

Further, a microphone can be positioned at any point along the ellipsoidal cavity 1030. For example, a microphone can be positioned proximate to and/or directed toward a focus point (e.g., focus point 1033, 1038), as shown in the left and right embodiments displayed in FIG. 10. As another example, a microphone can be positioned at and/or directed toward the approximate center of the ellipsoidal cavity 1030, as shown in the center embodiment displayed in FIG. 10.

The receiving device cavity 1040 in which a microphone 1045 is disposed can be substantially similar to the receiving device cavities described above. For example, a portion of the receiving device cavity 1040 can be configured, at least in part, as a channel through which at least a portion of the test gas and/or tested gas in the ellipsoidal cavity 1030 can flow. While all of the receiving devices shown in FIGS. 8-10 are disposed in the bottom portion of the sensor head, one or more receiving devices (and so also one or more receiving device cavities) can be disposed in the top portion of a sensor head.

Example embodiments provide a number of benefits. Examples of such benefits include, but are not limited to, compliance with one or more applicable standards (e.g., IP65, IEC 60079-28, Zone 1 or Zone 2 compliance), ease in maintaining and replacing components, and more accurate and quicker detection and measurement of impurities in gases.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A sensor head, comprising:
   a first piece, comprising:
   a body having an outer surface and an inner surface;
   a light source cavity disposed in the body at the inner surface, wherein the light source cavity is disposed at a first end of the body and is configured to receive a light source;
   an optical device cavity disposed in the body at the inner surface, wherein the optical device cavity is disposed adjacent to the light source cavity and is configured to receive an optical device;
   an ellipsoidal cavity disposed in the body at the inner surface, wherein the ellipsoidal cavity is disposed adjacent to the optical device cavity;
   a receiving device cavity disposed in the body adjacent to the inner surface that forms the ellipsoidal cavity, wherein the receiving device cavity is configured to receive a receiving device; and
   at least one channel disposed in the body, wherein the at least one channel has a first end disposed at the inner surface adjacent to the ellipsoidal cavity,
   wherein the light source cavity, the optical device cavity, the ellipsoidal cavity, the receiving device cavity, and the at least one channel are linearly aligned with respect to each other within the body.

2. The sensor head of claim 1, wherein the inner surface that forms the ellipsoidal cavity is optically and acoustically reflective.

3. The sensor head of claim 2, further comprising:
   a second piece coupled to the first piece, wherein the second piece is substantially symmetrical to the first piece, and wherein optically and acoustically reflective properties are substantially uniform on the inner surface forming the ellipsoidal cavity between the first piece and the second piece.

4. The sensor head of claim 1, wherein the at least one channel comprises a first channel that is configured to receive a test gas and deliver the test gas to the ellipsoidal cavity.

5. The sensor head of claim 4, wherein the at least one channel comprises a second channel that is configured to receive at least a portion of a tested gas from the ellipsoidal cavity.

6. The sensor head of claim 4, wherein the test gas flows from the ellipsoidal cavity through the receiving device cavity.

7. An optical gas sensor, comprising:
   at least one piece of a sensor head, wherein the at least one piece comprises:
   a body having an outer surface and an inner surface;
   a light source cavity disposed in the body at the inner surface, wherein the light source cavity is disposed at a first end of the body;
   an optical device cavity disposed in the body at the inner surface, wherein the optical device cavity is disposed adjacent to the light source cavity;
   an ellipsoidal cavity disposed in the body at the inner surface, wherein the ellipsoidal cavity is disposed adjacent to the optical device cavity, and wherein the ellipsoidal cavity comprises a first focus point and a second focus point;
   a receiving device cavity disposed in the body adjacent to the inner surface that forms the ellipsoidal cavity; and
   a first channel disposed in the body, wherein the first channel has a first end disposed at the inner surface forming the ellipsoidal cavity;
   a light source disposed within the light source cavity;
   an optical device disposed within the optical device cavity; and
   a receiving device disposed within the receiving device cavity,
   wherein the light source, the optical device, the ellipsoidal cavity, the receiving device, and the at least one channel are linearly aligned with respect to each other within the body of the at least one piece of the sensor head.

8. The optical gas sensor of claim 7, wherein the receiving device comprises a tuning fork, wherein the tuning fork comprises a plurality of tines that surround the second focus point within the ellipsoidal cavity.

9. The optical gas sensor of claim 8, further comprising:
   a power source coupled to the light source, wherein the power source provides power and control signals to the light source.

10. The optical gas sensor of claim 8, further comprising:
    a driver coupled to the tuning fork, wherein the driver causes tines of the tuning fork to vibrate at a resonant frequency.

11. The optical gas sensor of claim 8, further comprising:
    a receiver coupled to the tuning fork, wherein the receiver determines an oscillation amplitude of tines of the tuning fork, wherein the oscillation amplitude of the tines is caused by an amplitude of acoustic waves associated with a gas injected through the first channel into the ellipsoidal cavity.

12. The optical gas sensor of claim 8, wherein the plurality of tines is parallel to an axis that includes the first focus point and the second focus point.

13. The optical gas sensor of claim 8, wherein the receiving device cavity is positioned at the inner surface adjacent to the ellipsoidal cavity at a location between the first focus point and the second focus point, and wherein the receiving device cavity receives tested gas from the ellipsoidal cavity.

14. The optical gas sensor of claim 13, wherein the receiving device comprises a tuning fork, wherein the tuning fork is disposed within the receiving device cavity and outside the ellipsoidal cavity.

15. The optical gas sensor of claim 7, further comprising a second channel disposed in the body, wherein a second end of the second channel is positioned at the inner surface adjacent to the ellipsoidal cavity and is substantially aligned with the second focus point, and wherein the second channel receives tested gas from the ellipsoidal cavity.

16. The optical gas sensor of claim 15, wherein the receiving device comprises at least one microphone, wherein the at least one microphone is disposed within the receiving device cavity and abuts the inner surface that forms the ellipsoidal cavity.

17. The optical gas sensor of claim 16, wherein the at least one microphone is directed to a point within the ellipsoidal cavity between and inclusive of the first focus point and the second focus point.

18. The optical gas sensor of claim 7, wherein the optical device emits light received by the light source at the first focus point within the ellipsoidal cavity.

19. The optical gas sensor of claim 7, wherein the receiving device cavity is disposed adjacent to the ellipsoidal cavity at a second end of the body, wherein the second end is opposite the first end.

20. The optical gas sensor of claim 7, wherein the light source generates light having one wavelength of a plurality of wavelengths, wherein the one wavelength is based on the gas injected through the first channel into the ellipsoidal cavity.

* * * * *